United States Patent
Ueda et al.

[11] Patent Number: 5,865,957
[45] Date of Patent: Feb. 2, 1999

[54] METHOD FOR PRODUCING BUTYRALDEHYDES

[75] Inventors: Akio Ueda; Kuninori Sadaie, both of Okayama, Japan

[73] Assignee: Mitsubishi Chemical Company, Tokyo, Japan

[21] Appl. No.: 554,407

[22] Filed: Nov. 6, 1995

[30] Foreign Application Priority Data

Dec. 1, 1994 [JP] Japan .................................. 6-298590

[51] Int. Cl.[6] .............................. B01D 3/00; C07C 27/28; C07C 45/82
[52] U.S. Cl. ................................ 203/25; 203/27; 203/91; 203/DIG. 8; 568/492; 568/913; 568/914
[58] Field of Search ................................... 203/25, 27, 29, 203/91, DIG. 8; 568/492, 454, 913, 881, 491, 914, 449, 882

[56] References Cited

U.S. PATENT DOCUMENTS

| | | | |
|---|---|---|---|
| 4,871,879 | 10/1989 | Laird ................................. | 203/DIG. 6 |
| 4,986,885 | 1/1991 | Driscoll et al. .......................... | 203/73 |
| 5,035,776 | 7/1991 | Knapp et al. ............................ | 203/26 |
| 5,102,505 | 4/1992 | Sorensen . | |
| 5,110,990 | 5/1992 | Blessing et al. ......................... | 568/492 |
| 5,177,267 | 1/1993 | Morris et al. ............................ | 203/91 |
| 5,227,544 | 7/1993 | Thurman et al. . | |
| 5,426,238 | 6/1995 | Mori et al. . | |
| 5,458,739 | 10/1995 | Boucher et al. ......................... | 203/91 |

FOREIGN PATENT DOCUMENTS 4-273841  12/1992  Japan .

OTHER PUBLICATIONS

Olsen, John "Unit Processes and Principles of Chemical Engineering" pp. 1–3.

Chem. Ing. Tech. vol. 66 (1994), No. 7, pp. 916–923, Ernest Wiebus et al, "Die Grosstechnische Oxosynthese Mit Immobilisiertem Katalysator."

*Primary Examiner*—Virginia Manoharan
*Attorney, Agent, or Firm*—Oblon, Spivak, McClelland, Maier & Neustadt, P.C.

[57] ABSTRACT

A method for producing butyraldehydes, by separating and purifying mixed butyraldehyde products formed by hydroformylation of propylene, into n-butyraldehyde and isobutyraldehyde by using a distillation column, wherein the distillation column is operated under such conditions that the pressure at the top of the distillation column is within a range of from 0.001 to 0.5 kg/cm$^2$G, and the pressure at the bottom of the column is within a range of from 0.05 to 1.0 kg/cm$^2$G.

6 Claims, 3 Drawing Sheets

METHOD FOR PRODUCING BUTYRALDEHYDES

BACKGROUND OF THE INVENTION

1. Field of the Invention

The present invention relates to a method for producing butyraldehydes. Particularly, it relates to a method for separating and purifying mixed aldehyde products formed by hydroformylation of propylene into n-butyraldehyde and isobutyraldehyde by distillation.

2. Discussion of Background

A process which comprises hydroformylation of propylene to obtain mixed butyraldehyde products, separating the products by distillation into n-butyraldehyde and isobutyraldehyde, subjecting the obtained n-butyraldehyde to aldol condensation to obtain 2-ethylhexanal, which is further subjected to hydrogenation to obtain 2-ethylhexanol, or a process which comprises subjecting the n-butyraldehyde directly to hydrogenation to obtain n-butanol, has been world-widely practiced on an industrial scale.

As a conventional technique for separating butyraldehyde isomers, e.g. Japanese Unexamined Patent Publication No. 273841/1992 discloses a method wherein crude aldehyde products containing branched chain and straight chain aldehydes are distilled in a single distillation column to obtain three different product streams simultaneously. As the distillation conditions for this method, it is disclosed that the distillation column is operated at a temperature of from about 115° to 140° C. under such a pressure condition that the pressure at the top of the column is from 0.07 to 2.1 kg/cm$^2$G, and the Examples are carried out under a column top pressure of from 0.6 to 0.7 kg/cm$^2$G at a column bottom temperature of from 99° to 129° C., and the pressure at the bottom of the column is from about 1.08 to 1.42 kg/cm$^2$G as calculated from the vapor pressure of n-butyraldehyde.

Further, U.S. Pat. No. 5,227,544 discloses a method for producing 2-ethylhexanol of a high purity, which comprises adding a small amount of water to an aldehyde distillation column to hydrolyze an oligomer of isobutyraldehyde contained in the crude butyraldehyde and to recover its entire amount in the form of a monomer. Here, the temperature at the top of the aldehyde distillation column is described to be preferably from 70° to 90° C., and the pressure at the top of the column is from about 0.2 to about 1.3 kg/cm$^2$G, as calculated from the vapor pressure of isobutyraldehyde.

Such an aldehyde distillation column designed to separate n-butyraldehyde and isobutyraldehyde, requires a large plate number and a large amount of reflux, since the boiling points of aldehyde isomers to be separated are very close to each other, and reboiling is one of the sections which require the largest energy in the process.

Now, to discuss the heat balance of a process relating to unitization of exhaust heat, the process will be described as divided into a heat generating side and a heat consuming side.

Firstly, the heat generating side will be described with reference to literatures. INDICATIONS, Winter 1982/83 (The International Journal of Davy Mackee) discloses that a hydroformylation reaction is carried out at about 100° C. under about 20 atm by maintaining a uniform catalyst solution in a reactor using an aldehyde polycondensation product as a solvent in the presence of a rhodium catalyst and a triphenylphosphine ligand.

Further, an Example of Japanese Unexamined Patent Publication No. 242038/1990 discloses a method wherein a reaction is carried out at 100° C. in a completely mixing type reactor of a first stage using the same catalyst as used in INDICATIONS, and an unreacted gas is introduced in a bubbling column type reactor of a second stage to further conduct a reaction at 90° C. An Example of Japanese Unexamined Patent Publication No. 112733/1985 discloses a method wherein a hydroformylation reaction is carried out at 120° C. using a water-soluble rhodium-phosphine complex as a catalyst.

Furthermore, WO93/20034 discloses Examples wherein a condensation reaction of n-butyraldehyde using an aqueous NaOH solution as a catalyst, is carried out at a temperature of from 63° to 120° C., and Japanese PCT Publication No. 501483/1991 discloses Examples wherein a catalytic hydrogenation reaction of aldehydes is carried out at a temperature of from 120° to 125° C. Japanese Unexamined Patent Publication No. 39632/1983 discloses a gas phase hydrogenation process which is carried out at an outlet temperature of the reactor of 195° C. However, in such a high temperature reaction, reuse of the heat of reaction is easy, and the heat of reaction is effectively used e.g. for preheating water for a boiler or a hydrogenation step.

Now, the heat consuming side will be described. The main parts in the process where the recovered heat is used, include, for example, a distillation column for alcohol purification and an aldehyde distillation column for separating a n-butyraldehyde and isobutyraldehyde. In the distillation column, reboiling belongs to the heat consuming side, and at the same time, the condenser at the top dissipates the heat and thus may be regarded as belonging to the heat generating side.

In the distillation for purifying 2-ethylhexanol, it is common to employ a column top pressure within a range of from a few tens mmHgA to about 100 mmHgA. The column top temperature is from about 100° to 122° C., as calculated from the vapor pressure, and the column bottom temperature is still higher by about 10° to 30° C. than the column top temperature. The distillation for purifying n-butyl alcohol is carried out usually under a column top pressure at a level of atmospheric pressure, the column top temperature is about 118° C., and the column bottom temperature is still higher by about 10° to 30° C. than the column top temperature.

Thus, the temperature levels at the heat generating side and the heat consuming side are very close to each other, and it has heretofore been difficult to conduct heat recovery inexpensively by direct heat exchange.

The conventional aldehyde distillation column has been operated under a relatively high pressure condition as mentioned above in order to decompose and recover high boiling point substances in the mixed aldehyde products as valuable products and to increase the column top temperature by pressurizing to make the temperature difference from the cooling water large so as to reduce the heat conducting area of the column top condenser. Consequently, the column bottom temperature has been necessarily high, whereby the energy consumption at the time of reboiling is large, and it has been difficult to efficiently recover exhaust heat from other heat generating steps in the process.

SUMMARY OF THE INVENTION

Accordingly, it is an object of the present invention to provide a method which gives conditions for most effectively operating the aldehyde distillation column and which effectively utilizes exhaust heat of the process to reduce the energy cost.

The present inventors have conducted extensive studies on the above problems and as a result, have found that by operating the aldehyde distillation column under a lower pressure condition within a specific range, aldehydes having substantially the same purity as obtainable by the conventional method conducted under a relatively high pressure condition can be obtained in a state where the heat load is controlled to a low level, and the column bottom temperature can be maintained at a low level, whereby exhaust heat from other steps can effectively be recovered. The present invention has been accomplished on the basis of these discoveries.

Thus, the present invention provides a method for producing butyraldehydes, which comprises separating and purifying mixed butyraldehyde products formed by hydroformylation of propylene, into n-butyraldehyde and isobutyraldehyde by means of a distillation column, wherein the distillation column is operated under such conditions that the pressure at the top of the column is within a range of from 0.001 to 0.5 kg/cm²G, and the pressure at the bottom of the column is within a range of from 0.05 to 1.0 kg/cm²G.

DETAILED DESCRIPTION OF THE PREFERRED EMBODIMENTS

Figure 1A:
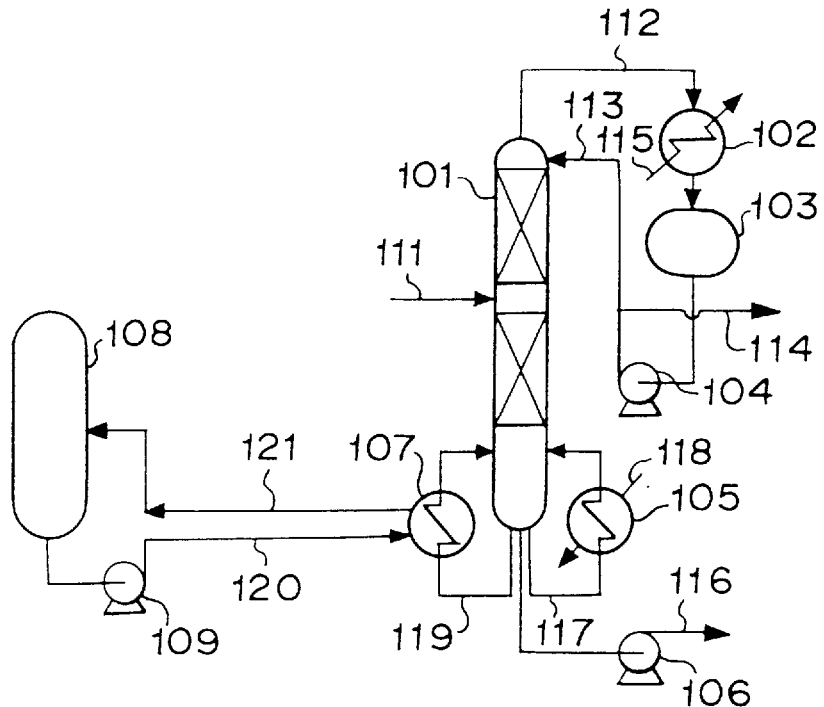
FIG. 1 is a flow chart for recovering exhaust heat from a hydroformylation reactor.

Now, the present invention will be described in detail.

The starting material propylene useful for the present invention, may be used usually without any special pretreatment. However, it is possible to employ the one having a sulfur content or a halogen content known as a catalyst poison or dienes, acetylenes or peroxides removed by a conventional method such as adsorption, extraction, distillation, heat treatment or separation by means of membranes.

As the catalyst for the hydroformylation, a rhodium catalyst having a trivalent organophosphorus compound as a ligand is usually employed. The trivalent organophosphorus compound may, for example, be a trivalent organophosphorus compound having an ability as a unidentate ligand or a multidentate ligand. The organophosphorus compound capable of serving as a unidentate ligand may be a tri-substituted phosphine, for example, a trialkylphosphine such as tributylphosphine or trioctylphosphine, a triarylphosphine such as triphenylphosphine, tritolylphosphine, or triphenylphosphine or tritylphosphine substituted by a sulfonic group or a halogen atom, a tricycloalkylphosphine such as tricyclohexylphosphine, an alkylarylphosphine such as monobutyldiphenylphosphine or dipropylphenylphosphine, a cycloalkylarylphosphine such as cyclohexyldiphenylphosphine, or an alkylcycloalkylphosphine such as cyclohexyldimethylphosphine. Further, it may, for example, be a trialkyl phosphite, a triaryl phosphite such as triphenyl phosphite or trinaphthyl phosphite which may have a substituent, or an alkylaryl phosphite.

The organophosphorus compound capable of serving as a multidentate ligand may, for example, be a bisphosphine compound such as 1,3-bis(diphenylphosphino)propane, a bisphosphine monoxide compound of the formula (1):

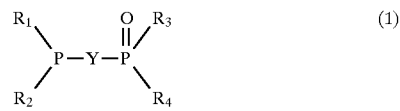

wherein each of $R^1$ to $R^4$ which are independent of one another, is an alkyl group, an aryl group, an alkyloxy group or an aryloxy group, and Y is a bivalent linking group, such as, bivalent hydrocarbon group which may have an oxygen atom, a sulfur atom or a nitrogen atom, or a bisphosphite compound.

These trivalent organophosphorus compounds may be used in combination as a mixture of two or more them as a ligand mixture, or a trivalent organophosphorus compound and a tetravalent organophosphorus compound such as triphenyl phosphine oxide may be used in combination.

As the rhodium source for the rhodium complex catalyst, an organic salt such as rhodium acetylacetonate or rhodium acetate, an inorganic salt such as rhodium nitrate, or an oxide such as rhodium oxide may also be used other than a rhodium complex such as hydride carbonyltris(triphenyl phosphine)rhodium or acetoxy bis(triphenyl phosphine) rhodium.

The above rhodium source may be supplied directly to the hydroformylation reactor. However, it is also possible that rhodium is reacted together with carbon monoxide, hydrogen and a trivalent organophosphorus compound in a solvent under a high temperature and pressure condition outside the reactor to preliminarily prepare a rhodium complex catalyst. The solvent to be used for the preparation of this catalyst is selected from solvents for reaction which will be described hereinafter, but it may not be the same solvent as the solvent for reaction. The preparation conditions are usually such that the rhodium concentration is from 1 wt ppm, to 2 wt %, the ratio of the trivalent organophosphorus compound to rhodium is P/Rh=10 to 10,000 (molar ratio), the temperature is from 60° to 200° C., the pressure is from atmospheric pressure to 200 kg/cm²G, and the treating time is selected within a range of from 5 minutes to 12 hours. The reaction system for the preparation of the catalyst may be a batch system or a continuous system.

As the solvent for the hydroformylation reaction, the olefin itself may be used, or the resulting aldehyde or high boiling point substances produced as by-products may be used as the solvent. Further, a solvent which is capable of dissolving the catalyst and which presents no adverse effects to the reaction, for example, an aliphatic hydrocarbon such as hexane or octane, an aromatic hydrocarbon such as toluene or xylene, an alcohol such as butanol, 2-ethylhexanol, ethylene glycol or propylene glycol, an ether such as triglyme, an ester such as dioctyl phthalate, or water, may also be used.

The hydroformylation reaction conditions are usually appropriately selected within such ranges that the hydrogen partial pressure is from 0.1 to 200 kg/cm², the carbon monoxide partial pressure is from 0.1 to 200 kg/cm², the total pressure is from 1 to 300 kg/cm²G, the ratio of hydrogen partial pressure/carbon monoxide partial pressure=0.1 to 10, the reaction temperature is from 60° to 200° C., the rhodium concentration (calculated as metal Rh) is from 1 wtppm to 2 wt %, the molar ratio of P (phosphorus atoms in the free organophosphorus ligand)/Rh=10 to 10,000, and the reaction time is from 5 minutes to 12 hours.

The hydroformylation reaction of propylene is conducted under the above formulation reaction conditions by continuously supplying the starting material olefin, oxo gas (carbon monoxide and hydrogen) and a catalyst liquid to a continuous type reactor. However, a batch system reactor may also be used. As the type of the reactor, an agitation tank type, a bubbling column type or a gas stripping type may, for example, be used.

The present invention is directed to define the distillation conditions at the time when n-butyraldehyde and isobutyraldehyde are separated by distillation from the mixed butyraldehyde products obtained as described above.

As such a distillation column, it is preferred to employ the one having a theoretical plate number of from about 40 plates to about 200 plates. When the distillation column is a tray column, it is preferred to employ the one having a real tray number of from 50 to 200 trays. Likewise, when the distillation column is a packed column, it is preferred that the column has a packing in a total height of the packing of from 15 m to 100 m. If the tray number or the height of the packing exceeds the above range, a large cost for steam for heating and unnecessary installation cost will be required, such being practically disadvantageous. Further, in a case where the distillation column is provided with both trays and packing in combination, if the total height satisfies the above-mentioned theoretical plate number, the column has an adequate ability for separation and purification.

The present invention is characterized in that as the distillation condition for the aldehyde distillation column, a relatively low pressure condition as compared with the conventional method is employed, i.e. the column top pressure is from 0.001 to 0.5 $kg/cm^2G$, preferably from 0.001 to 0.3 $kg/cm^2$, more preferably from 0.001 to 0.2 $kg/cm^2G$, and the column bottom pressure is from 0.05 to 1.0 $kg/cm^2G$, preferably from 0.05 to 0.8 $kg/cm^2G$, more preferably from 0.05 to 0.4 $kg/cm^2G$. According to the present invention, highly pure aldehyde isomers can be obtained in a state where the heat load is controlled to be low, and exhaust heat from other steps can effectively be recovered. If the column top or column bottom pressure of the above distillation column is too low, the heat conducting area of the condenser to be employed for condensing and liquefying the distillate will have to be enlarged, such being undesirable. On the other hand, if the column top or column bottom pressure of the distillation column is too high, the separation performance tends to be poor, and the heat source for distillation increases, such being undesirable.

Further, the difference between the pressure at the top and the pressure at the bottom of the distillation column (the pressure difference of the column) is usually from 0.05 to 0.4 $kg/cm^2$, preferably from 0.05 to 0.2 $kg/cm^2$, more preferably from 0.05 to 0.15 $kg/cm^2$. In order to bring the pressure difference in the column within this range, it is preferred to employ a packing as the internal of the distillation column. The temperature at the top of the column is usually from 60° to 74° C., preferably from 60° to 72° C., more preferably from 60° to 69° C. The temperature at the bottom of the column is usually from 76° to 98° C., preferably from 76° to 93° C. According to the present invention, by employing the pressure condition of the distillation column within the above specified range, it is possible to maintain the temperature at the bottom of the distillation column at a low level as compared with the conventional method, whereby it becomes possible to effectively recover exhaust heat from other heat generating steps in the process. The reflux ratio is usually from 20 to 50, preferably from 25 to 40.

The distillation column having the distillation condition defined by the present invention, is not particularly limited with respect to the distillation system so long as it is capable of directly separating n-butyraldehyde and isobutyraldehyde. The n-butyraldehyde separated by the method of the present invention may be directly hydrogenated to n-butanol, or may be subjected to an aldol condensation reaction by means of an alkali catalyst, followed further by a hydrogenation reaction to obtain 2-ethylhexanol.

The condensation reaction of n-butyraldehyde separated by the method of the present invention, can be conducted in either a liquid phase or a gas phase. In a case where the condensation reaction is conducted in a liquid phase, an aqueous alkali catalyst solution such as an aqueous sodium hydroxide solution is employed, the temperature is usually from 80° to 120° C., and the pressure is usually within a range of from atmospheric pressure to 6 $kg/cm^2G$, provided that it is at least the saturation pressure of the liquid at the set temperature. The condensation reactor may be a reactor of e.g. a plug type or a mixing tank type whereby mixing of the aldehyde and the catalyst contained in the aqueous phase is maintained uniformly.

The hydrogenation reaction can be conducted in either a gas phase or a liquid phase using a solid catalyst having a metal such as Ni, Cr or Cu supported thereon. The hydrogenation conditions are usually such that the temperature is from 60° to 200° C., and the hydrogen pressure is within a range of from 1 to 200 $kg/cm^2G$.

As mentioned above, according to the present invention, the temperature at the bottom of the aldehyde distillation column can be maintained at a relatively low level as compared with the conventional method, whereby it is possible to effectively recover exhaust heat from other heat generating steps in the process. Many embodiments may be mentioned as specific embodiments for recovery of such exhaust heat. Typical embodiments will be described below with reference to the drawings.

FIG. 1a shows a flow chart for recovering a part of the heat of reaction of a hydroformylation reactor 108 as a part of the reboiling heat for an aldehyde distillation column 101. The hydroformylation reaction solution is supplied to a reboiler 107 for heat recovery via a pipeline 120 by a pump 109 and heat-exchanged with the bottom liquid stream 119 of the aldehyde distillation column. The cooled hydroformylation reaction solution is recycled to the hydroformylation reactor 108 via a pipeline 121.

Figure 1B:
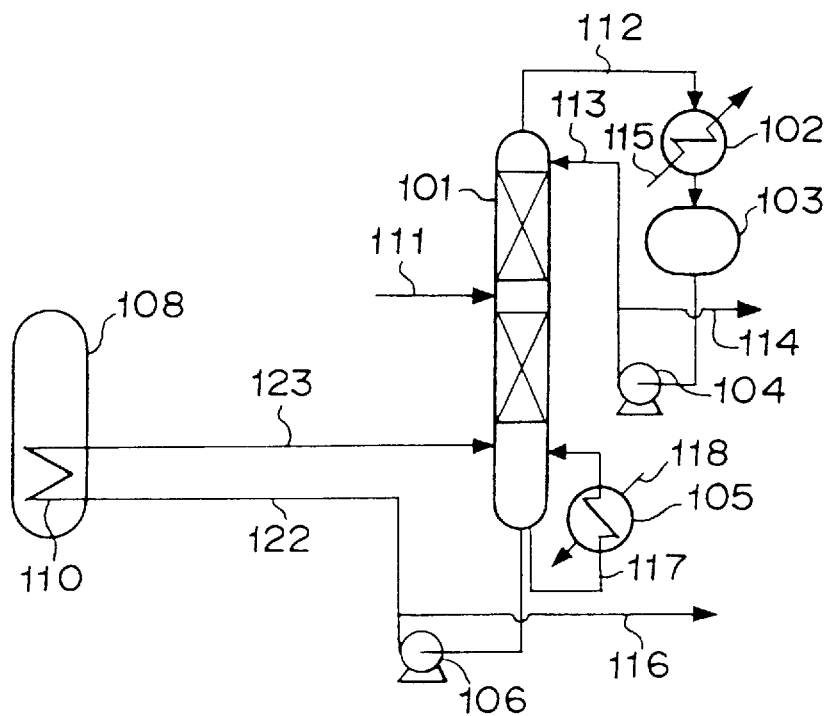

Similar heat recovery can be accomplished also in FIG. 1b. Namely, the bottom liquid of the aldehyde distillation column 101 is supplied for heat-exchange to a heat conducting zone 110 constituted by a group of coiled pipes provided in the interior of the hydroformylation reactor 108, via a pipeline 122 by a pump 106, whereby heat removal of the hydroformylation reactor 108 is carried out, and at the same time, the heated bottom liquid stream is recycled to the aldehyde distillation column 101 via a pipeline 123 to use it as reboiling energy for the aldehyde distillation column 101.

The systems illustrated in FIGS. 1a and 1b can be applied also to heat recovery from a condensation reactor. Namely, by using the reactor 108 as a condensation reactor, heat recovery from the condensation reactor to the aldehyde distillation column can be carried out.

Figure 2A:
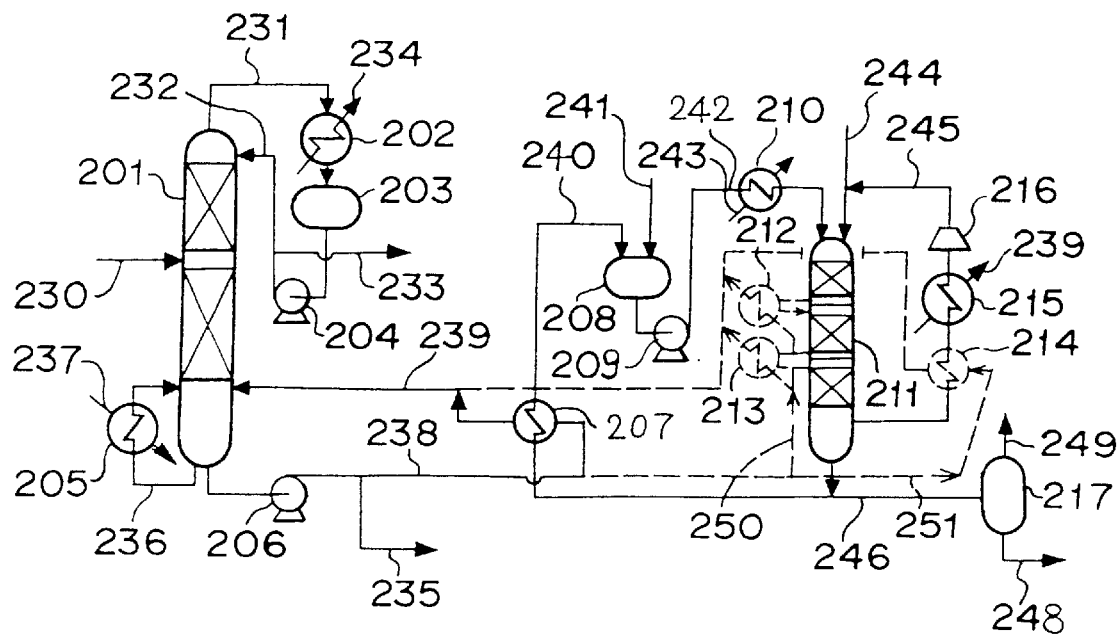
FIG. 2 is a flow chart for recovering exhaust heat from a hydrogenation process.

FIG. 2a illustrates an embodiment for the heat recovery from a liquid phase hydrogenation process. A starting material aldehyde stream 241 is charged together with a recycled alcohol solvent stream 240 into a receiving tank 208 and then charged into a hydrogenation reactor 211 by a pump 209. The hydrogenation reactor 211 is a fixed bed multistage reactor, whereby the reaction is carried out by parallel flow contact together with a starting material hydrogen gas stream 244 and a recycled hydrogen gas stream 245. A part of the reaction product liquid is used as a recycled alcohol solvent stream 240, and the rest is sent to a purification system by a pipeline 248 via a degassing tank 217. The hydrogen gas after the reaction is recycled to a recycling compressor 216. Removal of the heat of reaction is carried out by any one of or a combination of heat exchangers 214 and 215 provided in a recycled hydrogen gas line 245 and intermediate heat exchangers 212 and 213 for the reactor. The bottom liquid of the aldehyde distillation column 201 is supplied to a heat exchanger (any one of heat exchangers 207, 212, 213 and 214) via a pipeline 238 by a pump 206, and the heated aldehyde column bottom stream 239 is recycled to the aldehyde distillation column 201 and used as a part of the reboiling energy.

Figure 2B:
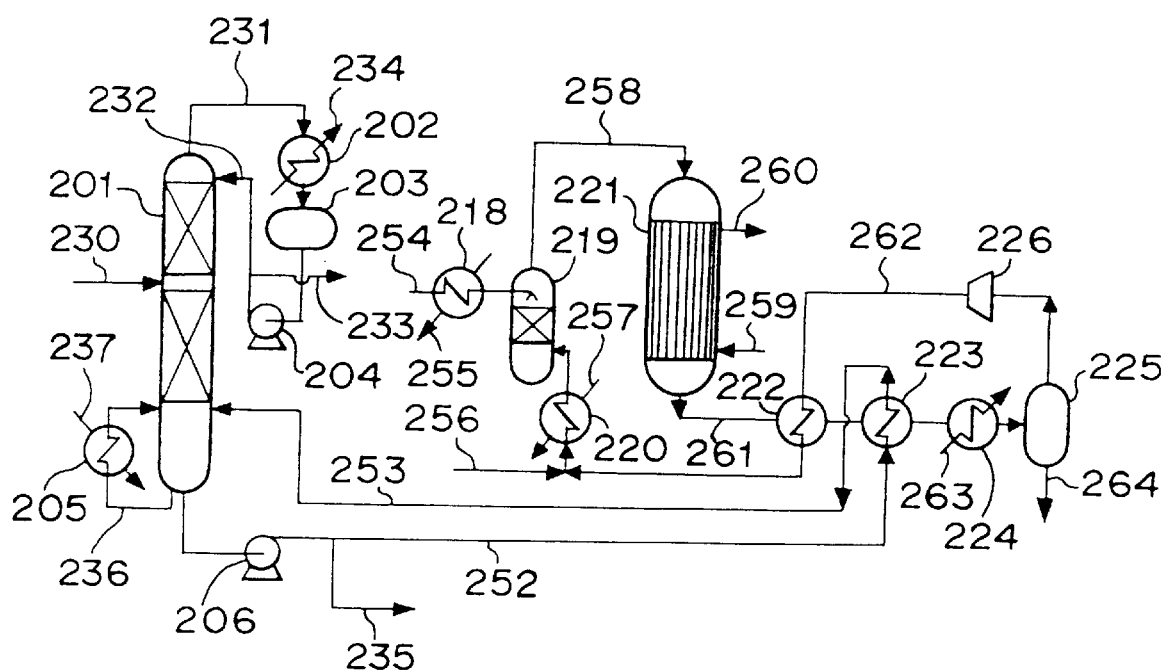

FIG. 2b illustrates an embodiment of the heat recovery from a vapor phase hydrogenation process. A starting material aldehyde 254, starting material hydrogen 256 and a recycled hydrogen stream 262 are heated by heat exchangers 218, 220 and 222 and supplied to a vaporizer 219. The starting material aldehyde is vaporized by the vaporizer 219 and supplied together with hydrogen gas to a hydrogenation reactor 211 via a pipeline 258. The hydrogenation reactor 211 is a multitubular fixed bed type, and the majority of the heat of reaction is removed by e.g. evaporation of boiler water 259 supplied to the shell side. A high temperature reaction product gas stream is cooled by a group of heat exchangers 222, 223 and 224, whereby a formed alcohol is liquefied. Gas-liquid separation is carried out by a separator 225, and the obtained crude alcohol is sent to a distillation system via a pipeline 264. The separated gas is pressurized by a recycling compressor 226 and recycled as a recycled hydrogen stream to the reactor. The bottom liquid of the aldehyde distillation column 201 is supplied to a heat exchanger 223 via a pipeline 252 by a pump 206, and the heated aldehyde column bottom stream 253 is recycled to the aldehyde distillation column 201 and used as a part of the reboiling energy.

Figure 3:
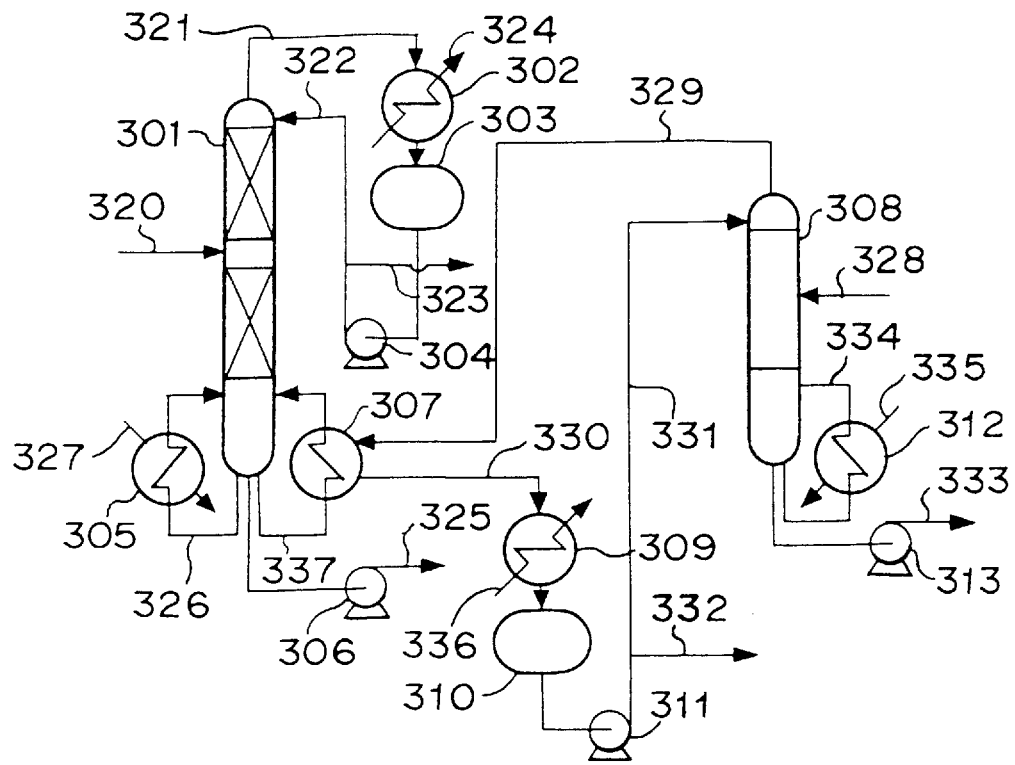
FIG. 3 is a flow chart for recovering exhaust heat from an alcohol distillation column.
Figure 3:
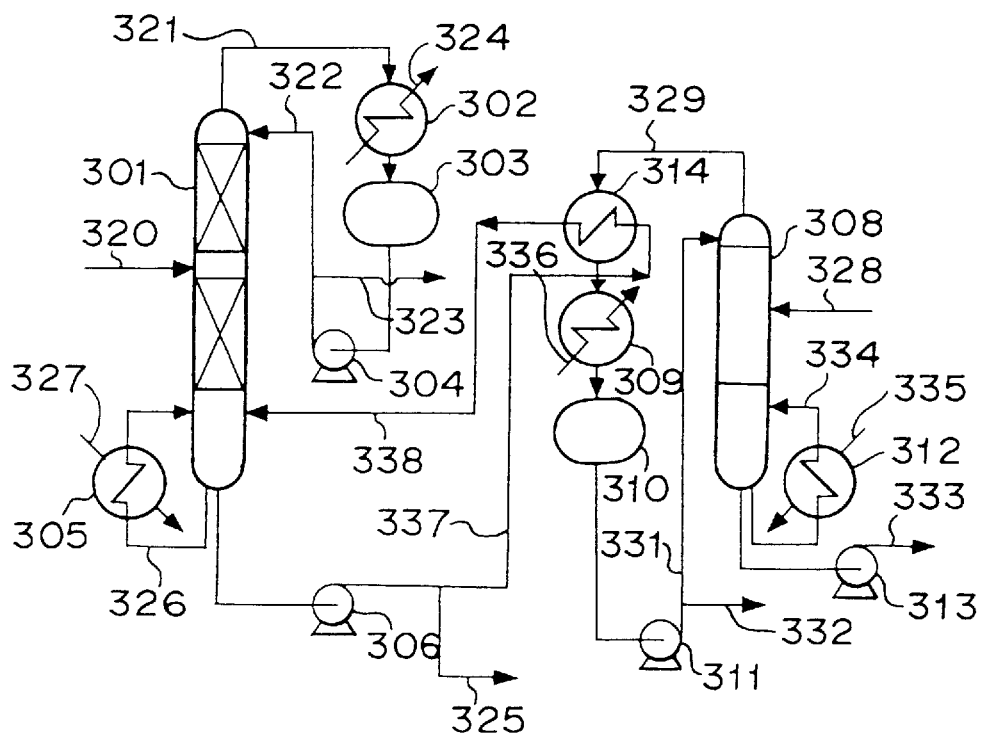

FIG. 3a illustrates an embodiment of the heat recovery from an alcohol distillation column. The column top vapor stream 329 of the alcohol distillation column 308 is led to a reboiler 307 for heat recovery of an aldehyde distillation column. In the reboiler 307 for heat recovery, condensation of the alcohol takes place on the shell side, while boiling of the aldehyde takes place on the tube side, and the latent heat of condensation of the alcohol is recovered as a part of the reboiling energy for the aldehyde distillation column 301. The alcohol stream 330 discharged from the reboiler 307 for heat recovery is further cooled by a condenser 309 for condensation and then led to a reflux tank 310. The condensed liquid is returned to the alcohol distillation column 308 as a reflux 331 and at the same time is withdrawn as a distillate stream 332.

Similar heat recovery can be achieved also by FIG. 3b. The bottom liquid of an aldehyde distillation column 301 is supplied to a first condenser 314 for an alcohol distillation column 308 via a pipeline 337 by a pump 306. The aldehyde stream 338 heated by the heat of condensation at the time when the column top gas stream 329 from the alcohol distillation column 308 is condensed in the first condenser 314, is recycled to the aldehyde distillation column 301 and used as a part of the reboiling energy. In a case where the condensation process is a process including a distillation column for the condensation product, the temperature condition for such a distillation column is equivalent to that for e.g. the alcohol distillation. Accordingly, the systems as illustrated in FIGS. 3a and 3b may be applicable to such a process.

In similar manners, various combinations may be employed for the heat recovery from fluids of 100° or higher in the process by considering their heat quantities. Further, exhaust heats of such a temperature level are present at various parts of chemical plants, and exhaust heats of adjacent plants may be widely taken into account for possible use.

The position for installing an installation for reboiling by exhaust heat is preferably below the feeding position and as close as possible to the bottom of the column.

Now, the present invention will be described in further detail with reference to Examples. However, it should be understood that the present invention is by no means restricted by such specific Examples.

In Examples, and Comparative Examples, a distillation column corresponding to a theoretical plate number of 70 plates was used by employing a conventional one column system whereby isobutyraldehyde is distilled from the top of the column, and n-butyraldehyde is obtained from the bottom of the column. The feeding position may be determined by a separate chemical engineering means from the feed composition, and is not limited to a specific position. However, for the purpose of identifying the differences of other conditions, this time, the feed was supplied to a position corresponding to a theoretical plate number of 33 plates from the top of the column. The feed liquid was supplied at a rate of 21.3 kg/hr, and it was composed of 11.02 wt % of isobutyraldehyde, 88.07 wt % of n-butyraldehyde, 0.89 wt % of water, 40 wt ppm of butanol and 0.02 wt ppm, of toluene.

COMPARATIVE EXAMPLE 1

Distillation was carried out under a pressurized condition of a conventional method i.e. under a column top pressure of 4 kg/cm$^2$G at a column top temperature of 115.8° C. (other conditions are given in Table 1), whereby the heat load for reboiling was 18.8 Mcal/hr, the column top composition was 96.90 wt % of isobutyraldehyde, and the column bottom composition was 99.93 wt % of n-butyraldehyde.

EXAMPLES 1 TO 5 AND COMPARATIVE EXAMPLES 2 AND 3

The distillation conditions were adjusted so that the compositions at the top and the bottom of the column would be equal to those in Comparative Example 1, and the results are shown in Table 1.

TABLE 1

|  | Comparative Example 1 | Comparative Example 2 | Comparative Example 3 | Example 1 | Example 2 | Example 3 | Example 4 | Example 5 |
|---|---|---|---|---|---|---|---|---|
| Internal | Tray | Tray | Tray | Tray | Tray | Packing | Packing | Packing |
| Column top composition: | | | | | | | | |
| IBD wt % | 96.90 | 96.90 | 96.90 | 96.90 | 96.90 | 96.90 | 96.90 | 96.90 |
| NBD wt % | 0.05 | 0.05 | 0.05 | 0.05 | 0.05 | 0.05 | 0.05 | 0.05 |
| Column bottom composition: | | | | | | | | |
| IBD wt % | 0.04 | 0.04 | 0.04 | 0.04 | 0.04 | 0.04 | 0.04 | 0.04 |
| NBD wt % | 99.93 | 99.93 | 99.93 | 99.93 | 99.93 | 99.93 | 99.93 | 99.93 |
| Reflux amount kg/h | 120.0 | 78.3 | 59.6 | 56.3 | 60.8 | 53.1 | 53.1 | 52.0 |
| Column top pressure kg/cm$^2$G | 4.0 | 2.0 | 0.6 | 0.08 | 0.08 | 0.08 | 0.08 | 0.001 |
| Column top temperature °C. | 115.8 | 96.1 | 74.8 | 63.1 | 63.1 | 63.1 | 63.1 | 60.8 |
| Column bottom pressure kg/cm$^2$G | 4.68 | 2.68 | 1.08 | 0.77 | 0.77 | 0.22 | 0.22 | 0.05 |
| Column bottom temperature °C. | 138.5 | 120.0 | 98.6 | 92.9 | 92.9 | 80.8 | 80.8 | 76.3 |
| Position of exhaust heat reboiler | Nil | Nil | Nil | Nil | 40 plates from the top | Nil | Column bottom | Column bottom |
| Temp. for exhaust heat reboiler level °C. | — | — | — | — | 86.0 | — | 80.8 | 76.3 |
| Recovered amount of exhaust heat Mcal/h | — | — | — | — | 1.0 | — | 1.0 | 2.0 |
| Heat load for reboiling Mcal/h | 18.8 | 12.0 | 8.6 | 7.8 | 7.4 | 7.3 | 6.3 | 5.0 |

IBD: isobutylaldehyde
NBD: n-butyraldehyde

Comparative Examples 2 and 3 illustrate a case where the operation conditions are adjusted towards a low temperature/low pressure direction to attain a situation preferable for heat recovery. Here, it has surprisingly been found that the separation performance is thereby improved, which is totally unexpected from the conventional method. However, even in Comparative Example 3 where the column top pressure is 0.6 kg/cm$^2$G, the column bottom temperature is about 99° C., which is not low enough to recover exhaust heat of other steps of a 100° C. level.

If the pressure was further reduced to a level of atmospheric pressure, as shown in Example 1, the heat load for reboiling became lower than ½ of Comparative Example 1. Further, the column bottom temperature was about 93° C. which is well below the temperature level of the exhaust heat of the process and thus belongs to a region within which recovery of exhaust heat is possible.

Therefore, at a position corresponding to a theoretical plate number of 40 plates from the top of the column, which is below the feeding position, reboiling was carried out by exhaust heat of the hydroformylation reaction step, an effect for saving reboiling energy corresponding to 40% of the recovered heat, was observed as shown by Example 2. In Examples 1 and 2, the column top temperature was about 63° C., and it is not desirable to further substantially reduce the column top pressure to a reduced pressure condition, since the temperature difference from the cooling water (usually from 30° to 35° C.) of the condenser tends to be small, and the heat conducting area of the condenser will have to be unduly large.

Therefore, the internal of the distillation column was changed from trays to a packing corresponding to a theoretical plate number of 70 plates, so that the column pressure difference was reduced to lower the column bottom temperature, and the results are shown as Example 3. As compared with Example 1, the reboiling heat quantity was reduced further by 6%, and the column bottom temperature was about 80° C., which is-more preferable for the heat recovery.

Further, when reboiling is carried out at the column bottom by exhaust heat of the hydrogenation reaction step, a decrease in the reboiling load equivalent to the recovered heat quantity was observed as shown by Example 4. Surprisingly, in Example 4, energy saving of more than 60% as compared with Comparative Example 1 was accomplished.

In Example 5, wherein the column top pressure and the column bottom pressure were further reduced, and reboiling was carried out by exhaust heat from the 2-ethylhexanol distillation step, the energy saving of more than 40% relative to Comparative Example 3 was accomplished, and the economical effects are substantial.

By operating an aldehyde distillation column under a low pressure condition within a specific range as defined by the present invention, aldehyde isomers of a high purity can be obtained in a state where the heat load is controlled to be low. Consequently, the column bottom temperature can be maintained at a low level as compared with the conventional method, whereby it becomes possible to effectively recover exhaust heat from other steps, which used to be difficult, and the energy cost can be saved. Thus, the value of the present invention for industrial application is high.

What is claimed is:

1. A process for reducing heat load in the production of butyraldehydes, which comprises:
   hydroformylating propylene to form mixed butyraldehyde products,
   recovering heat from the hydroformylating step,
   feeding said mixed butyraldehyde products to a distillation column equipped with a reboiling system, wherein the heat required for reboiling is the heat recovered from the hydroformylating step which is conveyed to the distillation column in the region between the bottom of the column and the point where mixed butyraldehyde products are fed into the distillation column, and
   separating and purifying said mixed butyraldehyde products into n-butyraldehyde and isobutyraldehyde, wherein the heat load is reduced by operating the distillation column conditions such that the pressure at the top of the column is within a range from 0.001–0.5 kg/cm$^2$G, and the pressure at the bottom of the column is within a range from 0.05–1.0 kg/cm$^2$G.

2. The process according to claim 1, wherein the pressure at the top of the column is within a range of from 0.001 to 0.3 kg/cm$^2$G, and the pressure at the bottom of the column is within a range of from 0.05 to 0.8 kg/cm$^2$G.

3. The process according to claim 1 wherein the distillation column is a packed column, and the difference between the pressure at the top of the column and the pressure at the bottom of the column is less than 0.2 kg/cm$^2$.

4. The process according to claim 1, wherein the temperature at the bottom of the distillation column is from 76° to 98° C.

5. A process for reducing heat load in the production of n-butanol, which comprises:

hydroformylating propylene to form mixed butyraldehyde products, recovering heat from hydrogenation of n-butyraldehyde or from a condensation portion of a distillation column in which n-butanol-product is distilled, feeding said mixed butyraldehyde products to the distillation column equipped with a reboiling system, wherein the heat required for reboiling is the heat recovered from the hydrogenation of n-butyraldehyde or the heat recovered from the condensation portion of the distillation column in which n-butanol product is distilled, separating and purifying said mixed butyraldehyde products into n-butyraldehyde and isobutyraldehyde, and subjecting the n-butyraldehyde obtained to hydrogenation thereby producing n-butanol, wherein said heat load is reduced by operating the distillation column under such conditions that the pressure at the top of the column is within a range from 0.001–0.5 kg/cm$^2$G, and the pressure at the bottom of the column is within a range from 0.05–1.0 kg/cm$^2$G.

6. A process for reducing heat load in the production 2-ethylhexanol, which comprises:

hydroformylating propylene to form mixed butyraldehyde products, recovering heat from hydrogenation of 2-ethylhexenal, from a condensation portion of a distillation column in which 2-ethylhexanol product is distilled or from a condensation reaction of n-butyraldehyde, feeding said mixed butyraldehyde products to the distillation column equipped with a reboiling system, wherein the heat required for reboiling is the heat recovered from the hydrogenation of 2-ethylhexenal, the heat recovered from the condensation portion of the distillation column in which 2-ethylhexanol product is distilled or the heat recovered from the step of the condensation reaction of n-butyraldehyde, separating and purifying said mixed butyraldehyde products into n-butyraldehyde and isobutyraldehyde, subjecting the n-butyraldehyde obtained to condensation reaction thereby preparing a condensation product, and subjecting the condensation product to hydrogenation thereby preparing 2-ethylhexanol, wherein said heat load is reduced by operating the distillation column under such conditions that the pressure at the top of the column is within a range from 0.01–0.5 kg/m$^2$G, and the pressure at the bottom of the column is within a range from 0.05–1.0 kg/cm$^2$G.

* * * * *